United States Patent [19]
Lievois et al.

[11] Patent Number: 6,076,049
[45] Date of Patent: Jun. 13, 2000

[54] NARROW BAND INFRARED WATER CUT METER

[75] Inventors: John S. Lievois; Roberto M. Lansangan, both of Houston; Mark E. Sudberry, Fort Worth, all of Tex.

[73] Assignee: Premier Instruments, Inc., Houston, Tex.

[21] Appl. No.: 09/031,098

[22] Filed: Feb. 26, 1998

[51] Int. Cl.[7] .................................................. G01N 22/00
[52] U.S. Cl. .................... 702/100; 73/61.44; 73/861.04; 324/637
[58] Field of Search ................................ 702/100, 45, 49, 702/50, 179; 73/61.44, 61.48, 861.04; 250/338.5, 343; 324/640, 637

[56] References Cited

U.S. PATENT DOCUMENTS

| | | | |
|---|---|---|---|
| 3,783,284 | 1/1974 | McCormack | 250/339 |
| 4,265,535 | 5/1981 | Pitt | 356/70 |
| 4,490,609 | 12/1984 | Chevalier | 250/269 |
| 4,492,862 | 1/1985 | Grynberg et al. | 250/255 |
| 4,628,204 | 12/1986 | Maes | 250/343 |
| 4,649,281 | 3/1987 | Schmitt et al. | 250/574 |
| 4,674,879 | 6/1987 | Gregorig et al. | 356/301 |
| 4,809,543 | 3/1989 | Baillie | 73/61.1 |
| 4,994,671 | 2/1991 | Safinya et al. | 250/255 |
| 5,035,581 | 7/1991 | McGuire et al. | 417/36 |
| 5,105,085 | 4/1992 | McGuire et al. | 250/343 |
| 5,107,118 | 4/1992 | Murray, Jr. et al. | 250/339 |
| 5,253,198 | 10/1993 | Birge et al. | 365/106 |
| 5,266,800 | 11/1993 | Mullins | 250/256 |
| 5,331,156 | 7/1994 | Hines et al. | 250/256 |
| 5,418,614 | 5/1995 | Brost et al. | 356/434 |
| 5,452,076 | 9/1995 | Schopper et al. | 356/128 |
| 5,567,318 | 10/1996 | Beall | 210/691 |
| 5,576,974 | 11/1996 | Marrelli et al. | 364/554 |
| 5,654,551 | 8/1997 | Watt et al. | 250/356.1 |

FOREIGN PATENT DOCUMENTS

2022933 C  11/1994  Russian Federation.

*Primary Examiner*—Kamini Shah
*Attorney, Agent, or Firm*—Akin, Gump, Strauss, Hauer & Feld, LLP

[57] ABSTRACT

The present invention provides a narrow band infrared water cut meter for detecting a full water cut range of a flow stream. The water cut meter includes a light source probe for irradiating the flow stream with a narrow band of infrared light and a light detector probe for sensing infrared light passed through the flow stream. For a narrow band of infrared light of a predetermined wavelength, there is a large difference in the absorption of infrared radiation between oil and water. At such a wavelength, the narrow band of infrared light is substantially transmitted through water content and gas content of the flow stream and substantially absorbed by oil content of the flow stream. The water cut meter thus differentiates oil by treating gas like water. Unlike other water cut meters, the narrow band infrared water cut meter is independent of variations of oil and water densities, salinity, oil emulsions, varying flow rates, and the gas content of a flow stream.

25 Claims, 13 Drawing Sheets

NARROW BAND INFRARED WATER CUT METER

BACKGROUND OF THE INVENTION

1. Field of the Invention

The present invention relates generally to water cut meters, and more particularly to a narrow band infrared water cut meter.

2. Description of the Related Art

Unbeknownst to most people outside the petroleum and petrochemical industries, the majority of oil wells around the world produce water along with oil. In fact, in the United States, the average production is 7 barrels of water for each barrel of oil. The average oil and water production of every well is a vital piece of information whose end users range from the field operators to the board room. For example, it is critical for operators to know the relative production of water and oil for each well for royalty allocations and to monitor individual well performance. Field superintendents review well performance to determine field remediation strategies in order to maintain or increase production. Reservoir engineers rely on well performance data to either design or evaluate the effectiveness of water flooding operations. Management looks at the overall field performance including historical oil productions to determine investment and divestment strategies.

In the United States alone, there are probably in excess of 700,000 producing oil wells, all of which are periodically tested for their production of oil, water and gas. Most states mandate this testing at regular intervals, but operators also need the data to properly manage the reservoir. In most cases, well testing will reveal the first signs of problems with a well indicating the need for workover or some form of other treatment.

Years ago, each well was connected to a test separator which would allow the operator to meter the produced oil, water and gas. With the advent of field unitization, a number of wells are now connected to a common production separator through a manifold. This configuration allows a well to be isolated from the combined flow and for diversion of that well flow to a test separator where the individual production of oil, water, and gas are measured.

There are approximately 40,000 test separators in operation today in the United States. In the majority of cases, these are two phase separators which separate the gas from the combined oil and water stream. In this scenario, flow meters measure the gas and combined liquid production. In addition, the operator has to obtain the percentages of the oil and water in the combined liquid stream to determine net oil and water production. This is commonly done by the time-consuming and expensive process of manual sampling or through the use of an online device called a water cut meter.

The other common variety of vessel-type separator is a three phase separator. This type of separator isolates the gas, oil and water so each phase can be metered independently. These separators are more expensive to own and operate and are considerably larger than the simpler two phase separators. In some cases, manual sampling is still used in the oil and water legs of a test separator due to inefficient separation or the propensity of certain oils to bind water in a tight emulsion.

Conventional water cut meters include capacitive water cut meters, density water cut meters, and microwave water cut meters. Capacitive, density and microwave water cut meters have particular limitations. Capacitive water cut meters are limited to detection of oil-water concentrations having a water cut equal to or less than roughly 10%. Over 95% of the oil wells in the United States have water cuts over 10%. While density water cut meters are able to detect a full range of oil and water concentrations (0–100% water cut), gas content of a flow stream prevents accurate water cut detection. Due to the low density of gas, a density water cut meter may view a small content of gas as a large content of oil. Microwave water cut meters, which are one of the more expensive types of water cut meters, are overly sensitive to water salinity and gas content. Also, microwave water cut meters are less accurate for oil-water concentrations on the high water cut end. Microwave water cut meters therefore would be undesirable for applications in which sensitivity is needed for oil-water concentrations on the high water cut end.

Examples of infrared-based sensors for "water cut" measurements are described in McGuire, U.S. Pat. No. 5,105,085, Gregorig, et al, U.S. Pat. No. 4,674,879, and Hines, U.S. Pat. No. 5,331,156. McGuire describes the use of an infrared light emitting diode and an opposing photodiode to determine the opacity of a flow composition. In McGuire, the output of the photodiode is compared to a range of preselected values roughly corresponding to different preselected opacities. The results of this comparison process are displayed by a light-emitting diode panel.

Gregorig describes the use of dual photodetectors to measure both direct and scattered signals in measuring the concentration of oil in water. The Gregorig technique involves directing a substantially monochromatic light beam through an oil/water mixture and measuring the relative intensities of light transmitted directly through the mixture and light scattered by the mixture. The direct and scattered output signals are then normalized by multiplying the signals by predetermined amplification factors. The direct output signal is represented by one equation, and the scattered output signal is represented by another equation.

In Hines, the optical density measurements of a flow stream are made by detecting photons of one predetermined energy where oil and water absorption characteristics are substantially identical and detecting photons of another predetermined energy where oil and water absorption characteristics are similar but not substantially identical. The difference in the absorption values is used to determine the oil and water fractions of a flow stream. Each predetermined energy level corresponds to a wavelength in a wavelength range between 1200 and 1900 nm.

SUMMARY OF THE INVENTION

Briefly, the present invention provides a narrow band infrared water cut meter for detecting a full water cut range of a flow stream. The water cut meter includes a light source probe for irradiating the flow stream with a narrow band of infrared light and a light detector probe for sensing infrared light passed through the flow stream. For a narrow band of infrared light of a predetermined wavelength, there is a large difference in the absorption of infrared radiation between oil and water. At such a wavelength, the narrow band of infrared light is substantially transmitted through water content and gas content of the flow stream and substantially absorbed by oil content of the flow stream. The water cut meter thus differentiates oil by treating gas like water. Unlike other water cut meters, the narrow band infrared water cut meter is largely immune to oil and water densities, salinity, oil emulsions, varying flow rates, and the gas content of a flow stream.

In a disclosed embodiment of the water cut meter, the light source probe houses an emitter and an offline backside detector, and the light detector probe houses an online forward detector and an offline forward detector. The offline forward detector is used to measure "scattering" by the flow stream, and the offline backside detector is used to measure "reflectance" by the flow stream. The online forward detector is used to measure transmission or absorption by the flow stream.

One disclosed application of the narrow band infrared water cut meter involves use of a gas liquid separator, flow meters, and the narrow band infrared water cut meter. The gas liquid separator separates gas from oil and water in a flow composition. The gas is provided to a gas flow meter, and the oil and water is provided to a liquid flow meter. Oil and water from the liquid flow meter is provided to the narrow band infrared water cut meter for detecting the water cut of the liquid composition. This application of a gas liquid separator, flow meters, and the narrow band infrared water cut meter provides for water cut detection in conjunction with gas-liquid separation.

Another application of the narrow band infrared water cut meter involves use of a flow meter and a pair of narrow band infrared water cut meters with each well line. Flow composition from a well line is provided to a first narrow band infrared water cut meter. A narrow band of infrared light having a first predetermined wavelength and emitted by the first narrow band infrared water cut meter is substantially transmitted through water content and gas content of the flow stream and is substantially absorbed by oil content of the flow stream. The flow composition from the first narrow band infrared water cut meter is provided to a second narrow band infrared water cut meter. A narrow band of infrared light having a second predetermined wavelength and emitted by the second narrow band infrared water cut meter is substantially transmitted through gas content of the flow stream and is substantially absorbed by the oil content and water content of the water stream. The flow composition from the second narrow band infrared flow meter is provided to a three phase mass flow meter for detecting the flow rate of the flow stream. This application of a narrow band infrared meter permits relatively inexpensive and accurate continuous three phase measurements at each well, permitting a large number of royalty allocation schemes.

A third application involves use of the narrow band infrared water cut meter to ensure the oil/water composition of overboard water is compliant with regulations governing the oil content of water discharged into an ocean. Overboard water refers to water which a water treatment facility (such as those present in some offshore drilling platforms) is allowed to discharge into an ocean. Before a flow composition is provided to a water treatment facility, the flow composition is provided to a narrow band infrared water cut meter. Narrow band infrared water cut meters may also be inserted before and/or after various stages of the water treatment process of the water treatment facility. The use of narrow band infrared water cut meters to verify water treatment and facilitate correction of any non-compliant flow compositions detected by the narrow band infrared water cut meters permits reduction of fines for non-compliance with oil content regulations.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
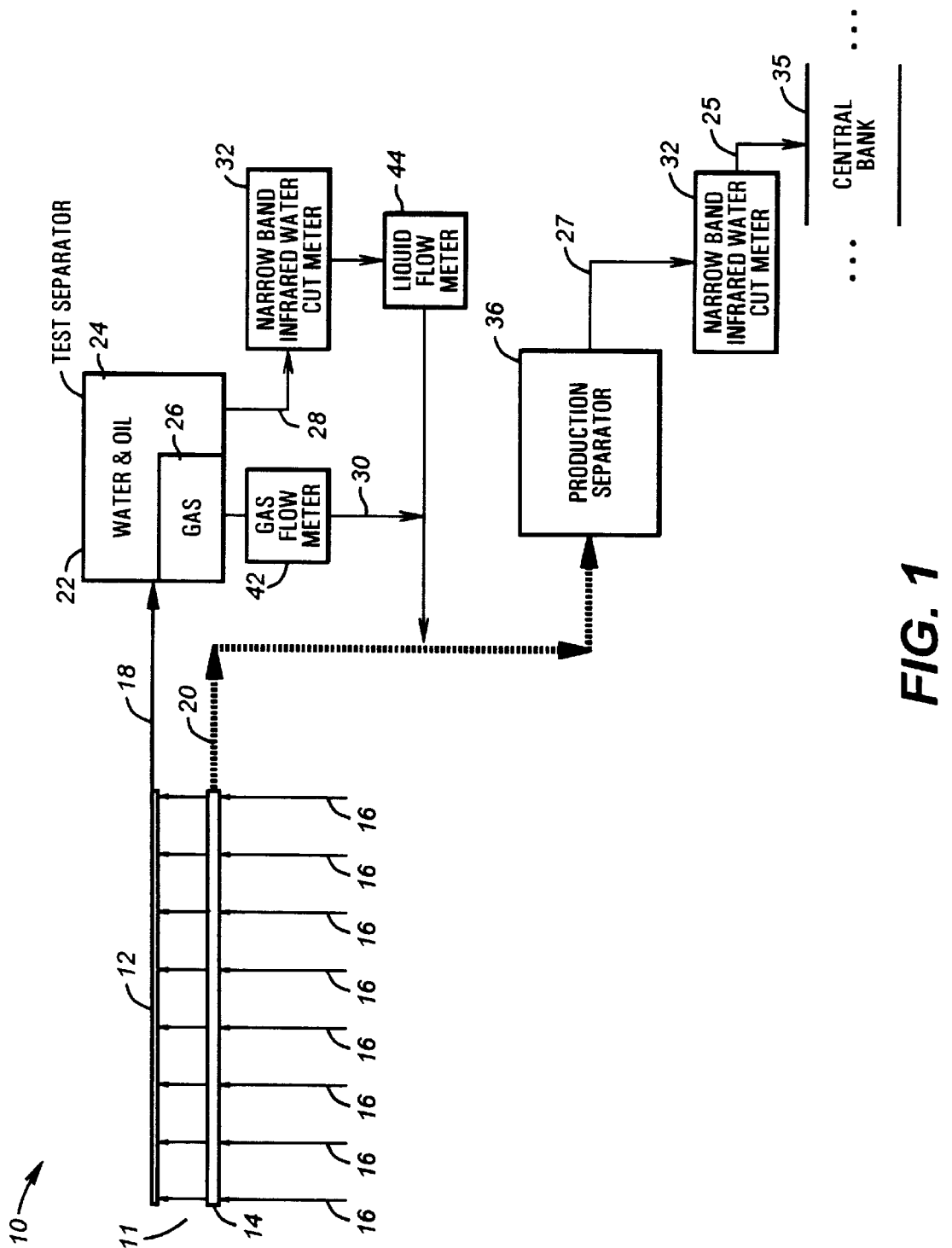
FIG. 1 is a schematic diagram of a satellite well testing configuration including a narrow band infrared water cut meter in accordance with the present invention.

Turning now to the drawings, FIG. 1 shows a satellite well testing configuration including a narrow band infrared water cut meter 32 in accordance with the present invention.

A well testing site or satellite is commonly used for gathering well lines for testing purposes.

One such testing purpose is a determination of a water cut of a flow composition for a well line. A water cut of a flow composition represents the percentages of oil and water of the flow composition. Water cut information may be used for a variety of purposes, which primarily include royalty calculations and reservoir management. A satellite or common gathering station 10 provides a test battery manifold 11 having a test line area 12 and a production line area 14 for receiving a plurality of well lines 16. The manifold 11 uses a series of valves (not shown) to direct one well line 16 at a time to the test line area 12 and to direct a plurality of well lines 16 to the production line area 14. The test line area 12 provides a test line 18 to a test separator 22. The test separator 22 may be either a two phase separator or a three phase separator which has been converted to a two phase separator. The test separator 22 includes a liquid region 24 for containing the water content and oil content of a flow composition and a gas region 26 for containing gas content of a flow composition.

The test separator 22 is of a type known in the art. A liquid leg 28 is provided from the liquid region 24 of the test separator 22 to the narrow band infrared water cut meter 32. As described more fully below in conjunction with FIGS. 5–12, the narrow band infrared water cut meter 32 detects the water cut of the liquid content provided by the liquid leg 28. The liquid content is provided from the narrow band infrared water cut meter 32 to a liquid flow meter 44 for measuring the volume of the liquid content. The liquid flow meter 44 may for example be a turbine meter known in the art. The liquid content is returned from the liquid flow meter 44 to the production line 20. The gas content from the gas region 26 of the test separator 22 is provided to a gas flow meter 42. The gas flow meter 42 may for example be a vortex or vortex shedding flow meter. As is understood in the art, a vortex flow meter uses fluid flow around a non-streamlined obstruction to create vortices that are formed and shed alternatively on either side of the obstruction. With a properly designed obstruction, or shedder bar, the vortices are formed and shed in proportion to the fluid velocity. The fluid flow rate may be inferred by measuring the rate of vortex formation. The gas content from the gas flow meter 42 is returned to the production line 20 through a return leg 30. The production line 20 goes to a production separator 36. The production separator 36 may also be of a type known in the art. The described well testing configuration provides for water cut detection using a two phase test separator. The narrow based water cut meter 32 here measures an "oil cut" (percentage of oil, without distinguishing water from gas), although the industry would still call the device 32 a water cut meter.

As an alternative to providing the narrow band infrared water cut meter 32 downstream of a test separator 32, the narrow band infrared water cut meter 32 may be provided downstream of a production separator 36. The production separator 36 provides a combined stream over a leg 27 to such a narrow band water cut meter 32. Unlike a narrow band meter 32 which may be provided between a test separator 22 and a liquid flow meter 44, the narrow band infrared water cut meter 32 provided downstream of the production separator 36 does not utilize a test separator or a test manifold. From this narrow band water cut meter 32, the combined stream is provided over a leg 25 to a central bank or battery 35. It should be understood that a plurality of production separators 36 may each provide a combined stream to the central bank 35.

Figure 2:
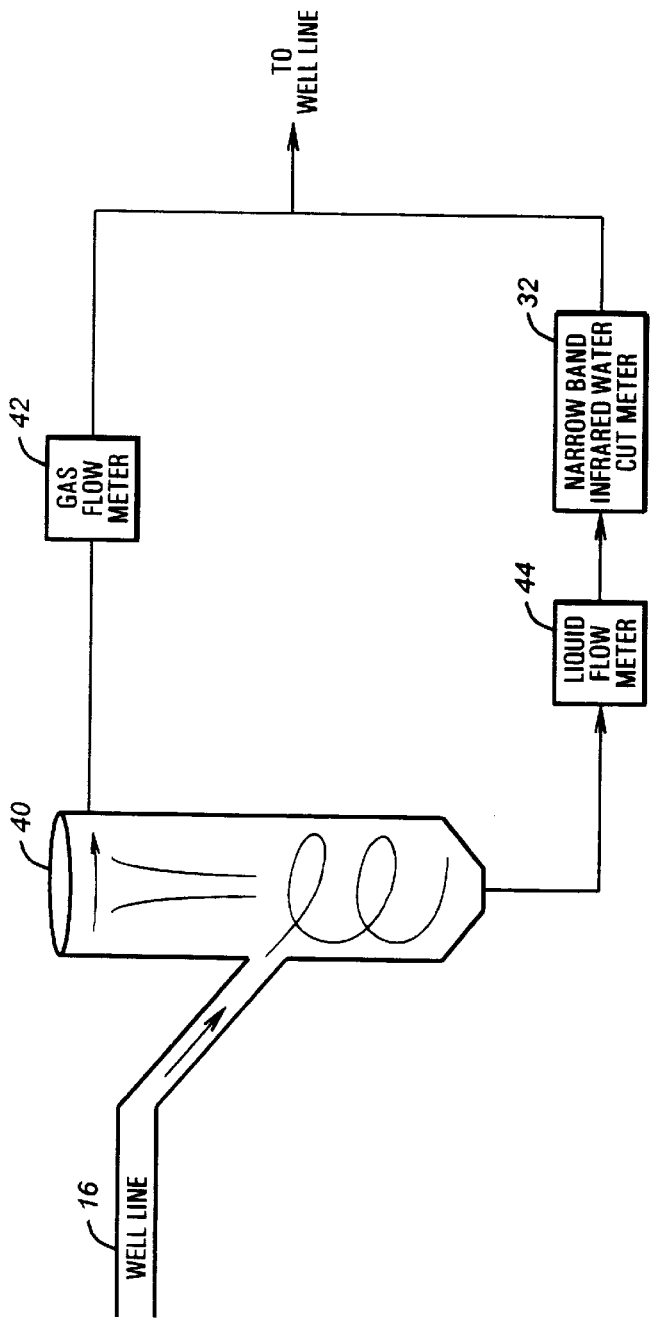
FIG. 2 is a schematic diagram of a well line testing configuration including a gas liquid separator and a narrow band infrared water cut meter in accordance with the present invention.

Referring to FIG. 2, a well line testing configuration including a gas liquid separator 40 and the narrow band infrared water cut meter 32 is shown. A well line 16 provides a flow composition having a gas content, oil content, and water content to a gas liquid separator 40. The gas liquid separator 40 is preferably a gas liquid compact cyclone separator (GLCC). The specific type of gas liquid separator, however, is not considered critical to the present invention. The gas liquid separator 40 serves to separate the gas content of the flow composition from the liquid content of the flow composition. Even when the gas liquid separator 40 achieves a high level of gas-liquid separation, liquid content typically includes a gas component referred to as gas carryover. Liquid content is provided from the gas liquid separator 40 to the liquid flow meter 44. Liquid content is provided from the liquid flow meter 44 to the narrow band infrared water cut meter 32. Gas carryover has typically complicated water cut detection by conventional water cut meters. As described below, the narrow band infrared water cut meter 32 differentiates between oil and gas by treating gas as water. In this way, the narrow band infrared water cut meter 32 does not mistake gas for oil. The gas content from the gas flow meter 42 and the liquid content from the narrow band infrared water cut meter 32 may be combined and returned to the well line 16. The described well line testing configuration, which represents another application of the narrow band infrared water cut meter 32, provides for water cut detection at the individual well line, eliminating the need for a test manifold or a test separator.

Figure 3:
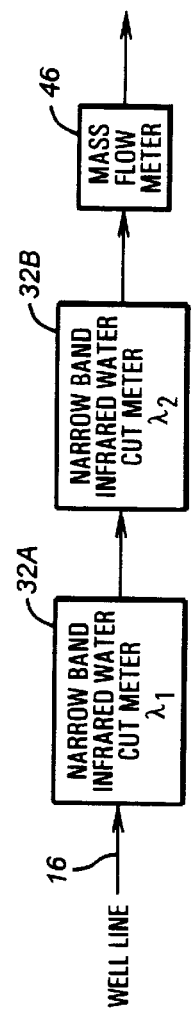
FIG. 3 is a schematic diagram of a three-phase well line testing configuration including a three phase flow meter and a pair of narrow band infrared water cut meters in accordance with the present invention.

Referring to FIG. 3, a three-phase well line testing configuration including a pair of narrow band infrared water cut meters and a mass flow meter is shown. The well line 16 provides a flow composition to a narrow band infrared water cut meter 32A. The water cut meter 32A emits a narrow band of infrared light having a predetermined wavelength $\lambda_1$ at which the infrared absorption properties of water and gas are similar and substantially different from the infrared absorption properties of oil. The water cut meter 32A thus serves to differentiate oil content from a combined water content and gas content. The water cut meter 32A provides the flow composition to a narrow band infrared water cut meter 32B. The water cut meter 32B provides a narrow band of infrared light having a predetermined wavelength $\lambda_2$ at which the infrared absorption properties of oil and water are similar and substantially different from the infrared absorption properties of gas. The water cut meter 32B thus serves to differentiate a combined oil content and water content from a gas content. For the disclosed embodiment, to calculate the volumetric flow rates for the three phases, either the absorption properties of water and gas at the predetermined wavelength $\lambda_1$ are the same or the absorption properties of oil and water at the predetermined wavelength $\lambda_2$ are the same. The water cut meter 32B provides the flow composition to a mass flow meter 46. The mass flow meter 46 serves to determine the total mass flow rate of the stream. With the total mass flow rate and the known densities of the three phases, the volumetric fractions for the three phases may be calculated. Like the well line testing configuration shown in FIG. 2, the described well line testing configuration provides water cut detection at the individual well line. An additional advantage of the described well line testing configuration is the capability for water cut detection without any separation of the flow composition. By taking water cut measurements of a flow composition without separation of the flow composition, the well testing configuration provides for simplified continuous well cut measurements.

Figure 4:
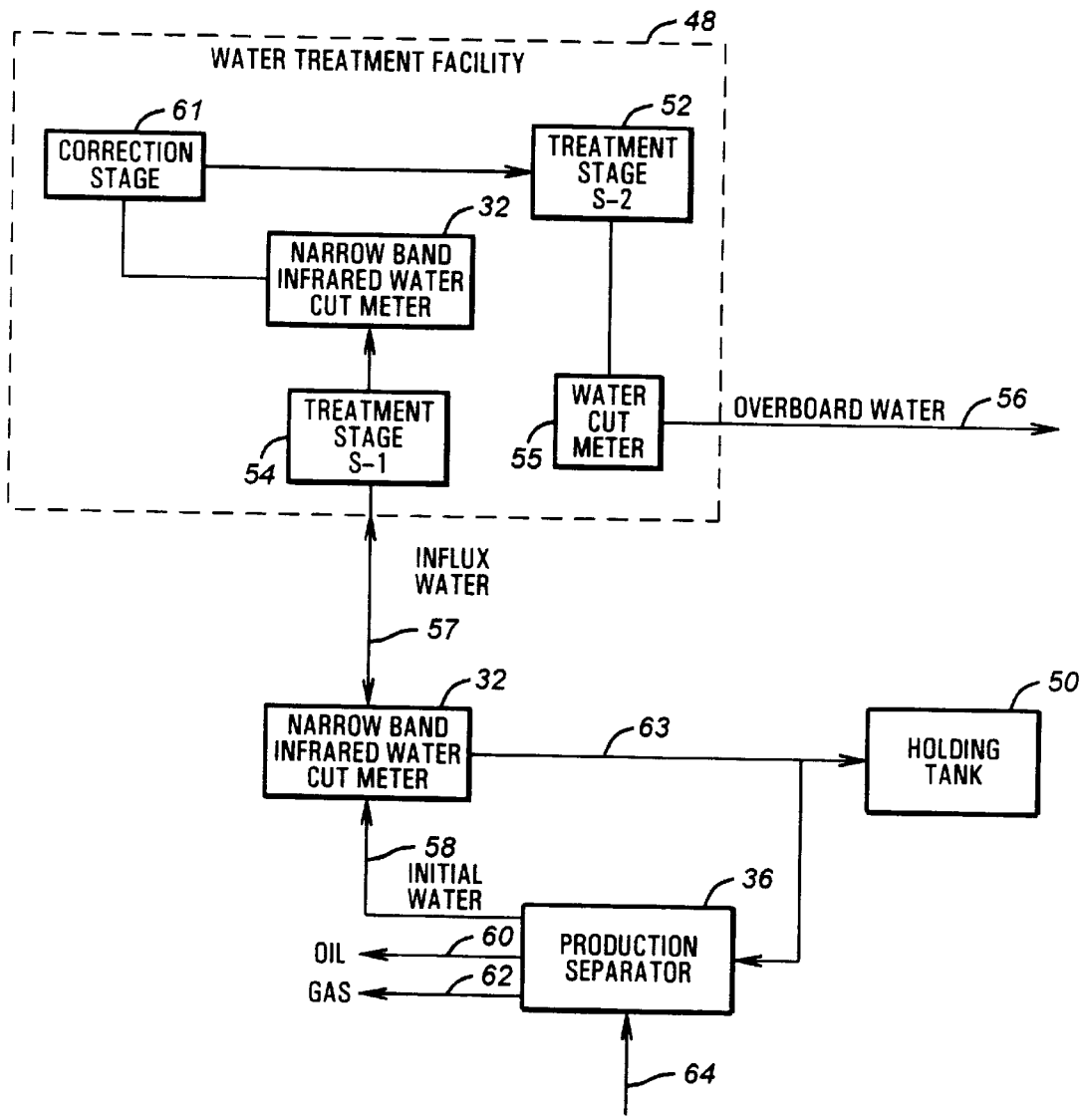
FIG. 4 is a schematic diagram of a water treatment verification configuration including a narrow band infrared water cut meter in accordance with the present invention.

Referring to FIG. 4, a water treatment verification configuration including the narrow band infrared water cut meter 32 is shown. A water treatment facility 48, such as those present in many offshore drilling or production platforms, is provided for treatment of water. The water treatment facility 48 may include a single or multiple water treatment stages. For example, the water treatment facility 48 is shown including a water treatment stage 52 and a water treatment stage 54. The end product of the water treatment facility 48 is overboard water 56. As overboard water 56 may be discharged into an ocean, the percentage of oil in the overboard water leg 56 is strictly regulated. If the overboard water 56 includes an oil concentration greater than a maximum oil concentration permitted by law, a fine is instituted against the company having control of the water treatment facility 48. The typical strategy for reducing the amount of fines to be paid by a company having control of the water treatment facility 48 has been to measure the oil concentration of the overboard water 56 and then adjust the water treatment process accordingly. For example, a water cut meter 55 is shown following the final treatment stage 52 of the water treatment facility 48 for determining the oil concentration of the overboard water 56.

In accordance with the present invention, the narrow band infrared water cut meter 32 may be used to periodically measure the oil concentration of initial water provided by an initial water leg 58 for direction to the water treatment facility 48. The initial water is provided to the narrow band infrared water cut meter 32 and the water cut meter 32 provides influx water along an influx water leg 57 to the water treatment facility 48. In this way, the oil concentration of water may be initially determined before the treatment process of the water treatment facility 48. If the oil concentration of the initial water is above the maximum oil concentration that can be handled by the water treatment facility, the initial water may be diverted through a return leg 63 back to a production separator 36 or to a holding tank 50. The production separator 36 receives a flow composition 64 and separates the flow composition 64 into the initial water provided through the initial water leg 58, oil content provided through an oil leg 60, and gas content provided through a gas leg 62. In practice, the main reason for excess oil in the overboard water 56 has been an upset at the production separator 36 resulting in a high concentration of oil in the initial water leg 58.

Alternatively or additionally, a narrow band infrared water cut meter 32 may be used to measure the oil concentration of water following a water treatment stage of the treatment process of the water treatment facility 48. In this way, immediately following a water treatment stage, oil concentration of water may be determined. A correction stage 61 for selectively adjusting the oil concentration of the water may be inserted into the water treatment process following the water cut meter 32. Given the typical concentrations of water to be measured for the water treatment facility 48, a path length, being the distance between an emitter 94 and an offline forward detector 96 (FIG. 6) of the narrow band water cut meter 32, may be increased to gain an exponential increase in sensitivity at the high water cut end.

The described water treatment verification configuration represents another potential application of the narrow band infrared water cut meter 32. It is contemplated that simple changes in the sensor configuration for the narrow band infrared water cut meter 32 described below may be adapted for numerous applications. Further, adjustments to the sensor model of the narrow infrared water cut meter 32 described below for particular field conditions may be made without detracting from the spirit of the present invention.

Figure 5:
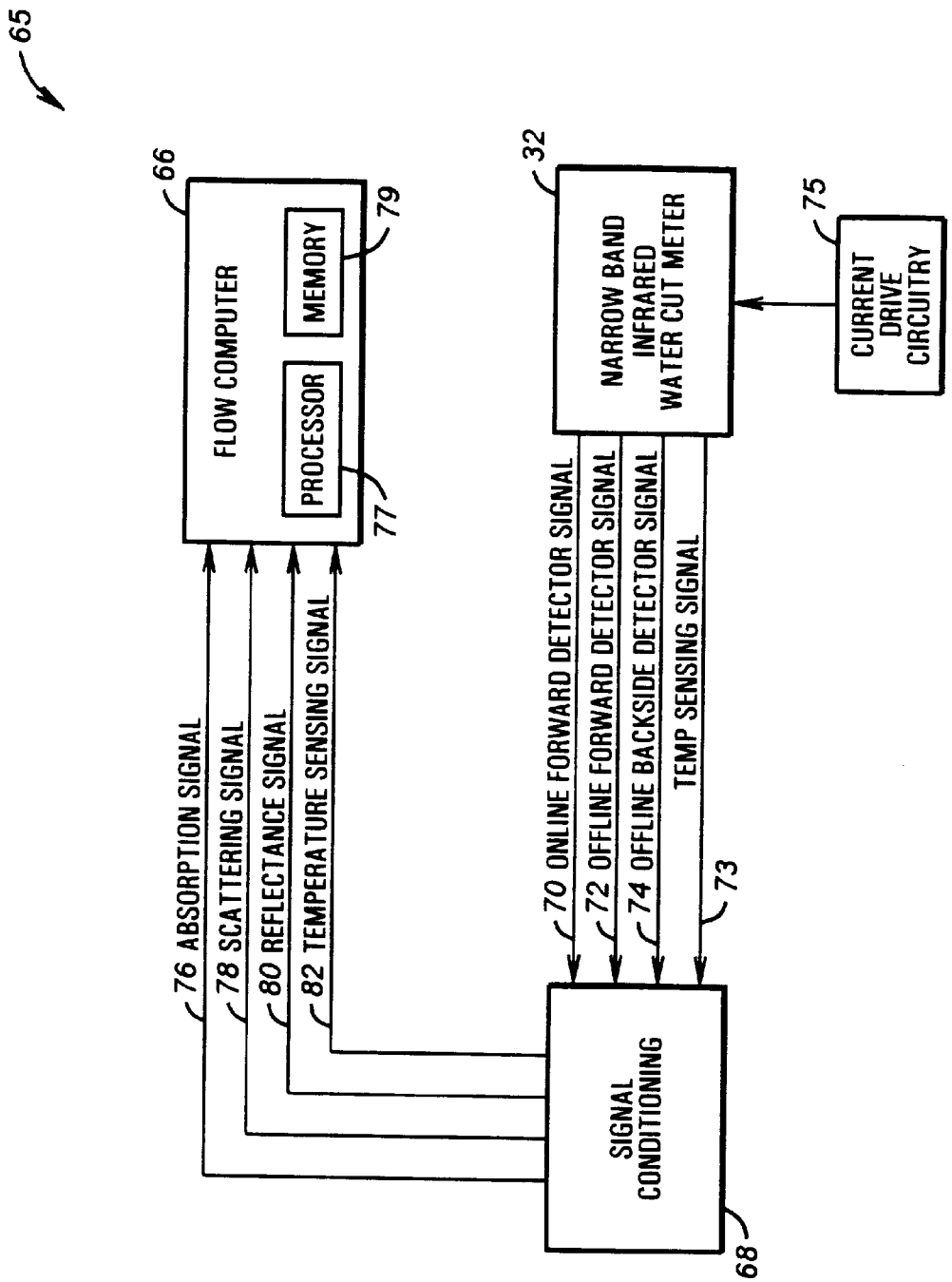
FIG. 5 is a schematic diagram of a narrow band infrared water cut meter system including a flow computer, a narrow band infrared water cut meter, signal conditioning block, and current drive circuitry in accordance with the present invention.
Figure 11:
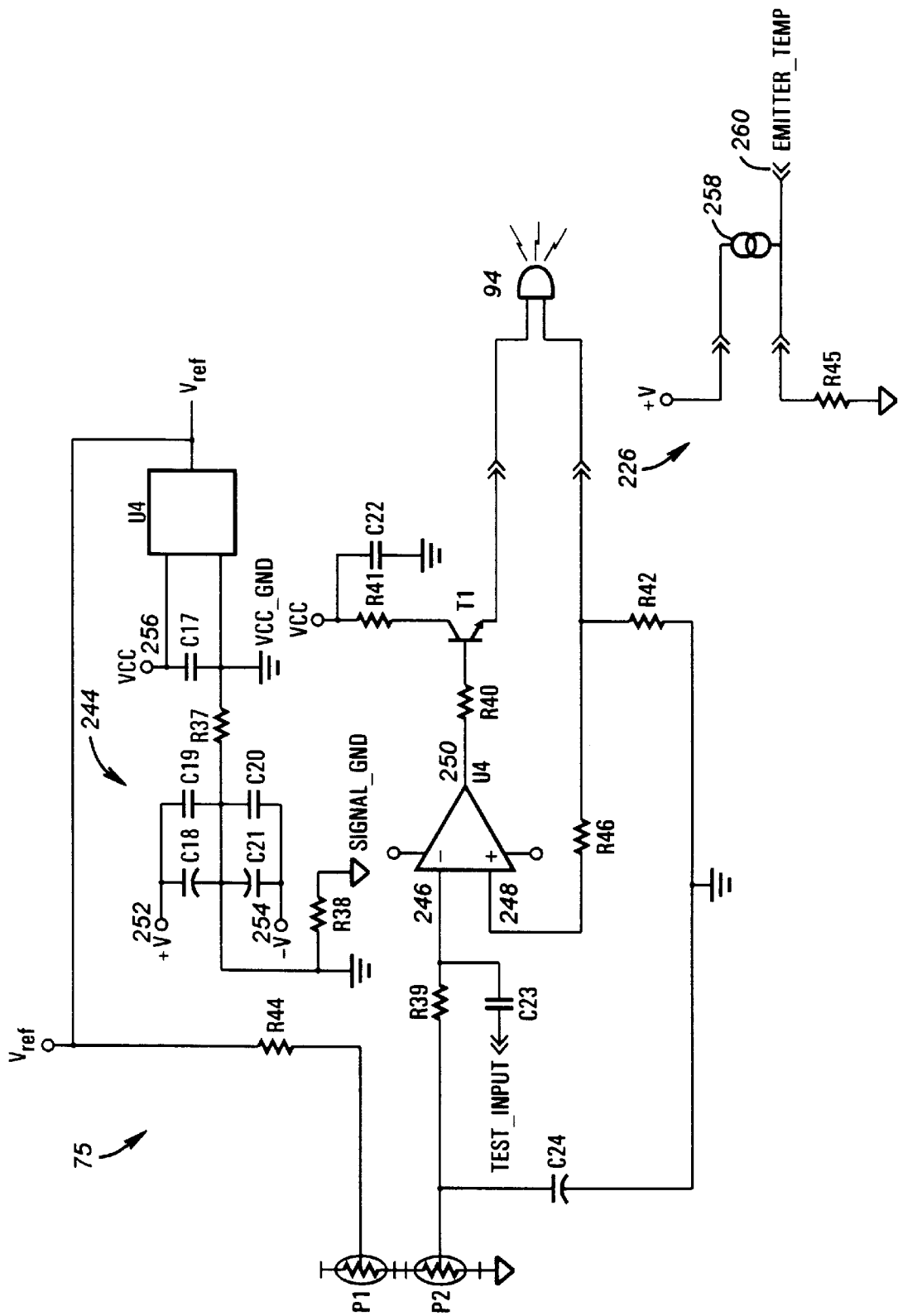
FIG. 11 is an exemplary circuit schematic of temperature sensing circuitry of FIG. 5 and the current drive circuitry of FIG. 5 for the emitter of FIG. 6.

Referring to FIG. 5, a narrow band infrared water cut meter system 65 is shown. The narrow band infrared water cut meter system 65 provides a flow computer 66, signal conditioning block 68, a narrow band infrared water cut meter 32, and current drive circuitry 75. The narrow band infrared water cut meter 32 includes the emitter 94 (FIG. 6) for emitting a narrow band of infrared light to the flow stream. The emitter 94 is driven by current drive circuitry (FIG. 11). The narrow band infrared water cut meter 32 may include the online forward detector 96, an offline forward detector 98, and an offline backside detector 100 (FIG. 6) for detecting attenuation of the narrow band of infrared light by a flow stream. The narrow band infrared water cut meter 32 alternatively may provide the online forward detector 96 as its single detector. The online forward detector 96 produces an online forward detector signal 70 representing absorption of the narrow band of infrared light; the offline forward detector 98 produces an offline forward detector signal 72 representing "scattering" of the narrow band of infrared light; and the offline backside detector 100 produces an offline backside detector signal 74 representing "reflectance" of the narrow band of infrared light. "Scattering" generally refers to infrared light traveling in a forward direction other than by a direct path, as opposed to the technical definition of scattering. "Reflectance" generally refers to infrared light traveling in a reverse direction other than by a direct path.

The online forward detector signal 70, the offline forward detector signal 72, a temperature sensing signal 73, and the offline backside detector signal 74 are provided to the signal conditioning block 68 for conditioning (or processing) the detector signals. The signal conditioning block 68 provides an absorption signal 76, a scattering signal 78, a reflectance signal 80, and a temperature sensing signal 82 to the flow computer 66. The absorption signal 76 is the output of online forward detector signal conditioning circuitry 220 (FIG. 8); the scattering signal 78 is the output of offline forward detector signal conditioning circuitry 222 (FIG. 9); and the reflectance signal is the output of offline backside detector signal conditioning circuitry 224 (FIG. 10). The flow computer 66 is of a conventional type and serves to interpret the absorption signal 76, scattering signal 78, reflectance signal 80, and temperature sensing signal 82. The temperature sensing signal 82 is the output of the temperature sensing circuitry 226 (FIG. 11) for sensing the temperature of the emitter 94 (FIG. 6).

Figure 6:
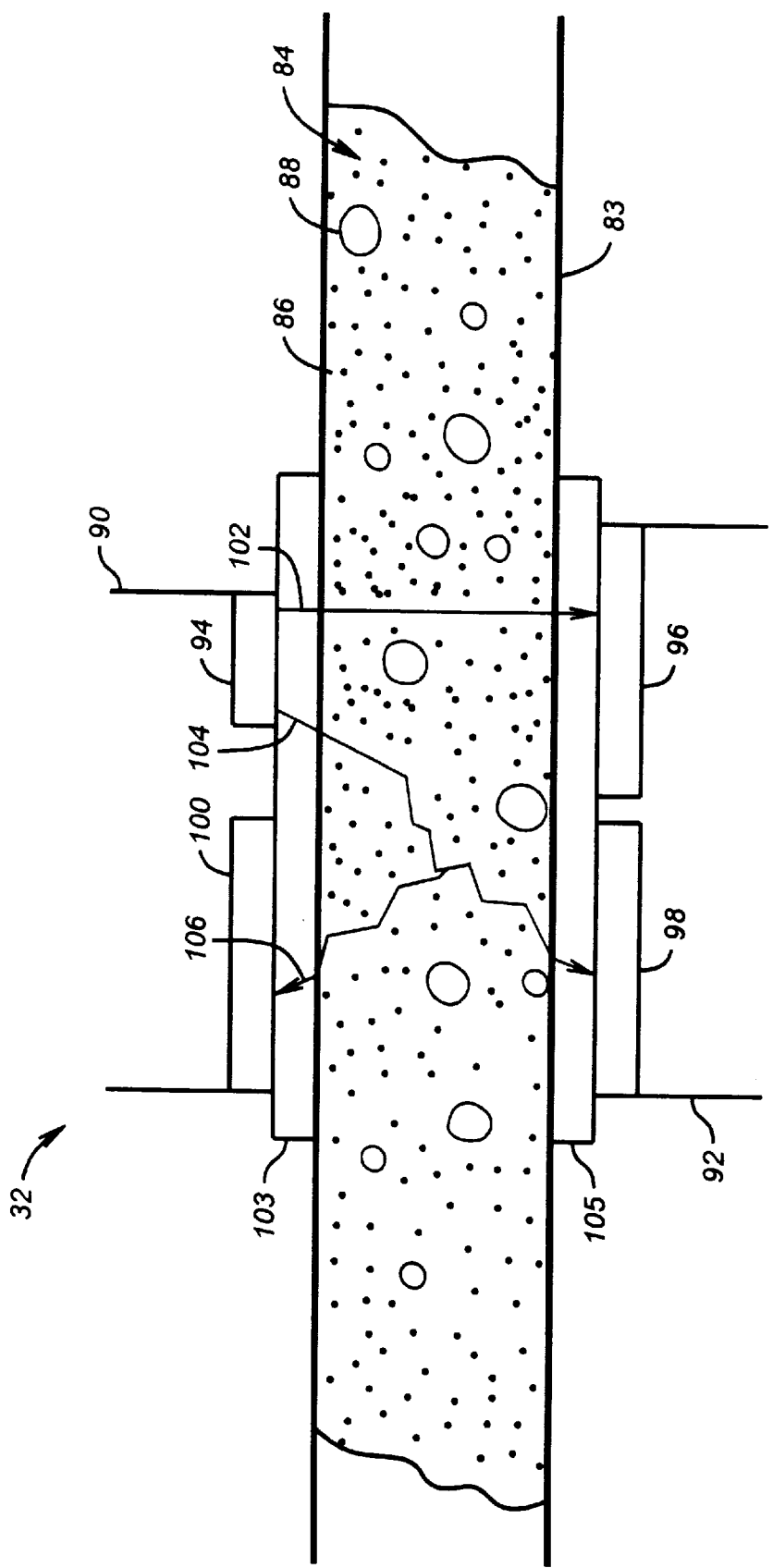
FIG. 6 is a schematic view of sensor components of the narrow band infrared water cut meter of FIG. 5 in relation to a flow stream through a pipeline with portions of the pipeline broken away.

Referring to FIG. 6, a schematic view of sensor components of the narrow band infrared water cut meter 32 in relation to a flow stream 84 is shown. The illustrated embodiment of the narrow band infrared water cut meter 32 includes a light source probe 90 and a light receiver probe 92. The light source probe 90 houses the emitter 94 for emitting a narrow band of infrared light to the flow stream 84 and an offline backside detector 100 for detecting "reflectance" of a narrow band of infrared light. In the illustrated example, light beams 102 and 104 are emitted by the emitter 94, and light beam 106 is detected by the offline backside detector 100. The light receiver probe 92 houses an online forward detector 96 for detecting absorption of a narrow band of infrared light and an offline forward detector 98 for detecting "scattering" of a narrow band of infrared light. In the illustrated example, light beam 102 is detected by the online forward detector 96, and the light beam 104 is detected by the offline forward detector 98. For shielding purposes, both the light source probe 90 and the light receiver probe 92 are separated from the flow stream 84 by glass windows 103 and 105 which may be sealed to the body of the probes 90 and 92.

The sensor components of the narrow band infrared water cut meter 32 are preferably placed on a pipeline 83 containing the flow stream 84. The pipeline 83 is shown with portions broken away to illustrate the relationship between the flow stream 84 and the water cut meter 32. A static mixer (not shown) may be placed upstream of the narrow band infrared water cut meter 32 in order to mix the flow stream 84 for increasing the accuracy of measurements by the narrow band water cut meter 32. The flow stream 84 includes continuous media 86 which is typically water and non-continuous media 88 which is typically oil.

Figure 7A:
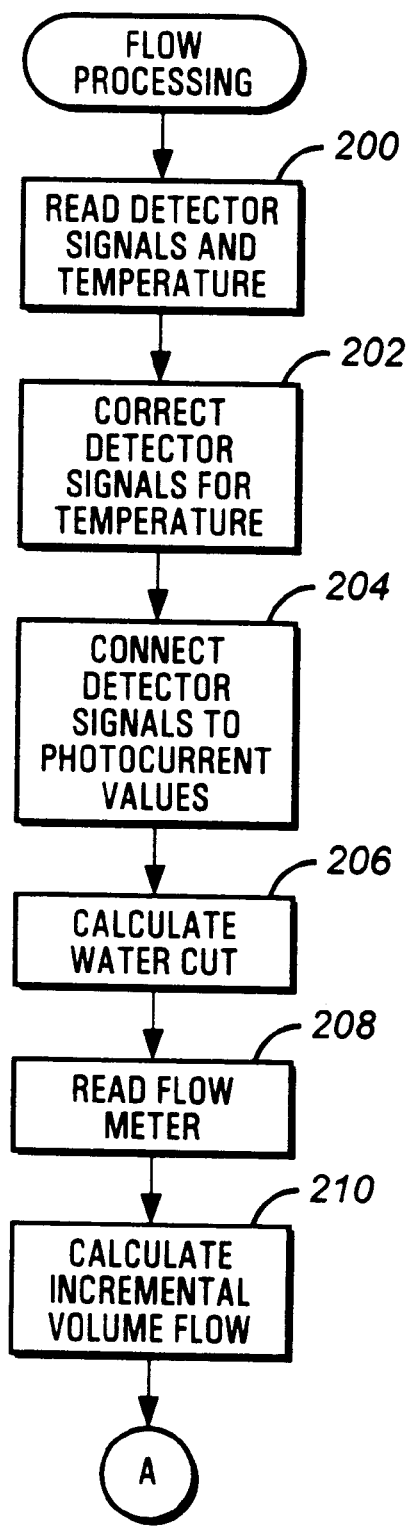
FIGS. 7A and 7B are flow charts of the flow processing technique performed by the flow computer of FIG. 5 for determining water cut of a flow stream with the narrow band infrared water cut meter of FIG. 5 in accordance with the present invention.
Figure 7B:
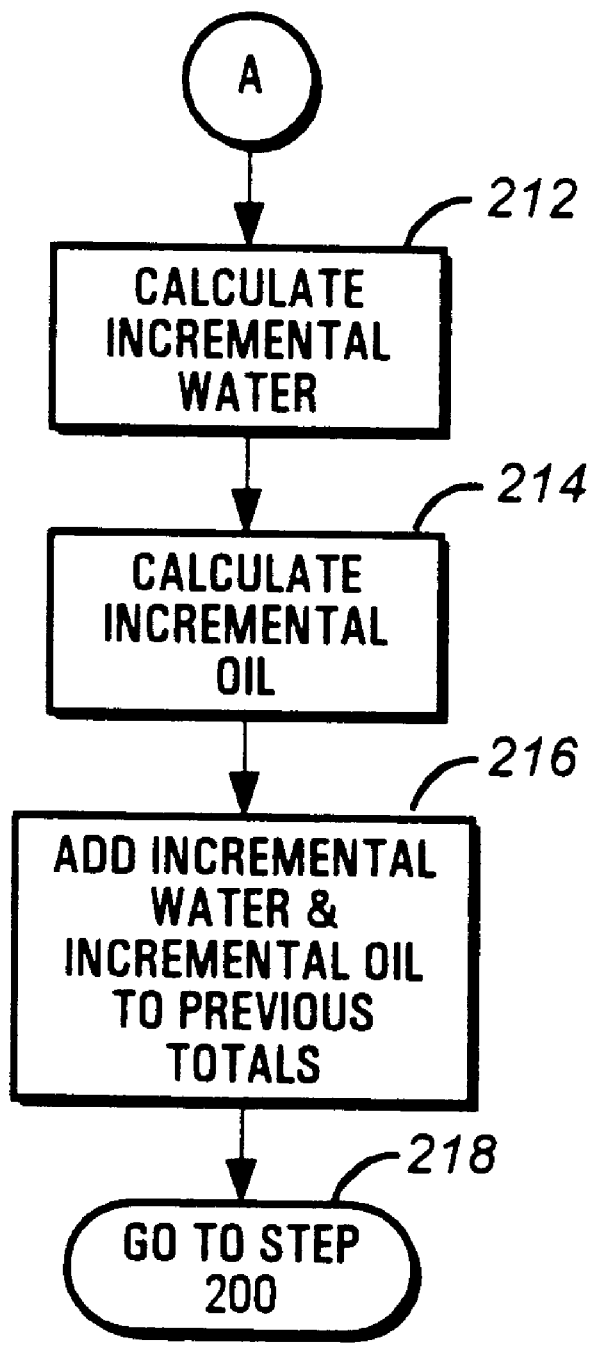

Referring to FIG. 7A and 7B, flow charts of the flow processing technique performed by the flow computer 66 (FIG. 5) for determining water cut with the narrow band infrared water cut meter 32 are shown. The flow computer 66 includes a processor readable medium 79 such as a memory for storing code executed by the processor 77 to perform the flow processing technique. Control begins at step 200 where the detector signals 70, 72 and 74 and temperature sensing signal 82 are read by the flow computer 66. From step 200, control proceeds to step 202 where the detector signals are corrected for temperature of the emitter 94 provided by the temperature sensing signal 82. Following is an exemplary equation which may be used for correcting the detector signals for temperature:

Corrected Signal [Detector Signal][1.2331−0.00303T].

The variable "T" in the above equation represents the temperature of the emitter 94 in degrees Fahrenheit. A temperature correction is important since the output of the emitter 94 varies with temperature. Next, in step 204, the corrected detector signals are converted to photocurrent values. Following is an exemplary equation which may be used for converting the corrected detector signals to photocurrent values:

Photocurrent=Corrected Signal−Amplified Gain Resistor.

Each detector signal is associated with signal conditioning circuitry having an amplifier gain resistor. The resistance value of the amplifier gain resistor is used in the above equation for converting the detector signal to a photocurrent value. From step 204, control proceeds to step 206 where the water cut of the flow stream 84 is calculated. The water cut of the flow stream 84 is calculated by a non-homogeneous linear equation which includes detector photocurrent values, an absorption constant, and hardware constants. Following is an exemplary equation which may be used for calculating the water cut ($C_W$):

$C_W$=A Log (Online Forward Detector Photocurrent+(B●Offline Forward Detector Photocurrent))+C.

In the above equation, A represents an absorption constant determined based on a pure oil absorption measurement and a pure water absorption measurement; B represents a geometric hardware constant for the offline forward detector 98; and C represents a general hardware calibration constant. If the backside detector photocurrent is greater than a reference backside detector photocurrent, Offline Backside Detector Photocurrent$_{ref}$, then the term D ● (Offline Backside Detector Photocurrent−Offline Backside Detector Photocurrent$_{ref}$) is added to the water cut equation. The Offline Backside Detector Photocurrent$_{ref}$ represents a photocurrent value of the offline backside detector 100 for a flow stream free of emulsions. The offline backside detector calibration constant, D, is empirically determined.

The values of the calibration constants or coefficients permit the narrow band water cut meter 32 to take into account any emulsions in the flow stream 84, the flow rate of the flow stream 84, and any entrained gas within the flow stream 84. Further, the water cut, $C_W$, is a value between 0 and 1, 0 representing 0% water and 1 representing 100% water. In accordance with the present invention, a water cut calculation is simplified by accounting for each detector signal in a single equation.

Control next proceeds to step 208 where a pulse input is measured by a liquid flow meter 46 (FIGS. 1 and 3). Next, in step 210, an incremental volume flow is calculated based on the pulse input detected by the flow meter 46. From step 210, control proceeds to step 212 (FIG. 7B) where an amount of incremental water is calculated. This amount may be calculated by multiplying the incremental volume by the calculated water cut, $C_W$. Control next proceeds to step 214 where an amount of incremental oil is calculated. The amount may be calculated by multiplying the incremental volume by (1−$C_W$). Next, in step 216, the calculated amount of incremental oil and the calculated amount of incremental water may be totaled with any previous incremental oil and incremental water measurements. In step 218, control returns to step 200 where the detector signals 70, 72, and 74 and temperature sensing signal 82 are again read. The flow processing technique thus provides continuous water cut calculations.

Figure 8:
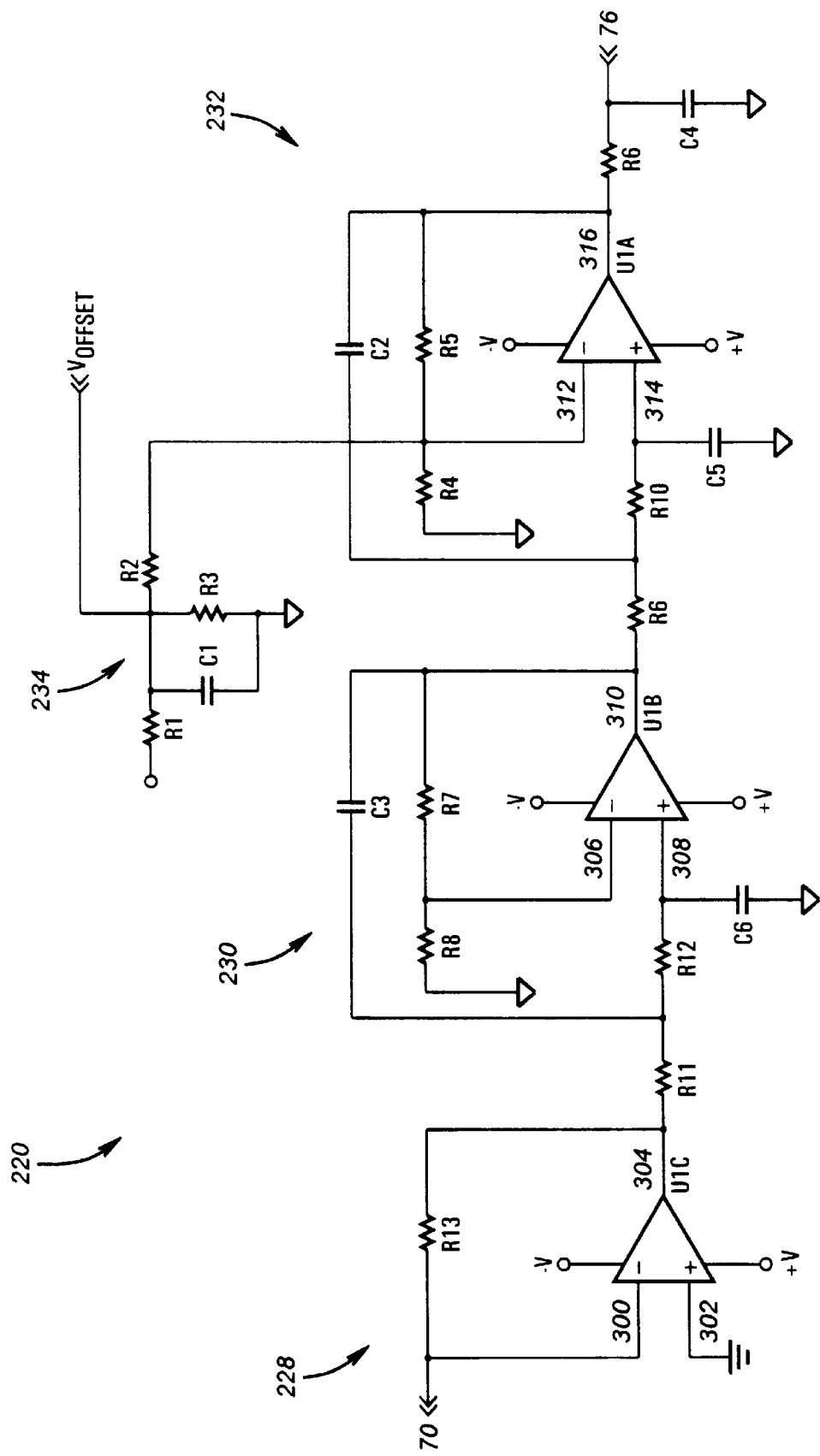
FIG. 8 is an exemplary circuit schematic of the signal conditioning circuitry of FIG. 5 for the online forward detector of FIG. 6.

The signal conditioning block 68 (FIG. 5) includes online forward detector signal conditioning circuitry 220 (FIG. 8), offline forward detector signal conditioning circuitry 222 (FIG. 9), and offline backside detector signal conditioning cicruitry 224 (FIG. 10). Referring to FIG. 8, an exemplary circuit schematic of signal conditioning circuitry 220 for the online forward detector 96 is shown. The input signal to the signal conditioning circuitry 220 is the online forward detector signal 70. The online detector signal 70 is provided to an inverting terminal 300 of an operational amplifier U1C which uses current-to-voltage conversion to measure a short circuit current of the online forward detector 96. A feedback network containing a feedback resistor R13 is provided between the inverting terminal 300 and the output terminal 304 of the operational amplifier U1C. Further, the non-inverting terminal of the operational amplifier U1C is coupled to ground.

The current-to-voltage conversion stage 228 is followed by a low pass filter stage 230. In the disclosed embodiment, the low pass filter stage 230 provides a fourth order Bessel low pass filter having a gain of four in the pass band and a cutoff frequency of approximately 0.2 hertz. The illustrated embodiment of the low pass filter stage 230 includes an operational amplifier U1B and an operational amplifier U1A, both having a capacitive and resistive feedback network. The non-inverting terminal 308 of the operational amplifier U1B is coupled to a capacitor C6 and a resistor R12. The resistor R12 is series coupled to a resistor R11 which serves as a connection between the current-to-voltage conversion stage 228 and the low pass filter stage 230. The inverting terminal 306 is coupled to the common node between a feedback resistor R7 and a feedback resistor R8. Feedback resistor R8 is also coupled to ground. A feedback capacitor C3 is coupled between the output terminal 310 and the common node between resistors R11 and R12.

The non-inverting terminal 314 of the operation amplifier U1A is coupled to an input capacitor C5 and an input resistor R10. The input resistor R10 is further coupled to a resistor R9 coupled to the output terminal 310 of the operational amplifier U1B. An inverting terminal 312 of the operational amplifier U1A is coupled to a feedback network 232 and offset circuitry 234. In the disclosed embodiment, the offset circuitry 234 ensures that the output of the signal conditioning circuitry 220 does not become negative. The offset circuitry 234 includes a resistor R2 and a resistor R3 in a shunt relationship, both resistors being coupled to an offset voltage $V_{offSet}$. The offset circuitry 234 further includes a resistor R1 serially coupled to the resistor R2 and a capacitor C1 in a parallel relationship with the resistor R3. Both the resistor R3 and the capacitor C1 are coupled to ground.

The feedback network 232 includes a feedback resistor R5 and a feedback resistor R4 coupled to the inverting terminal 312 of the operational amplifier U1A. The feedback resistor R4 is also coupled to ground, and the feedback resistor R5 is also coupled to the output node 316. The feedback network 232 also includes a feedback capacitor C2 coupled between the output node 316 and a node defined between resistor R9 and resistor R10. The output node 316 is further coupled to a resistor R6 which is coupled to a capacitor C4 and a node forming the output signal 76.

Figure 9:
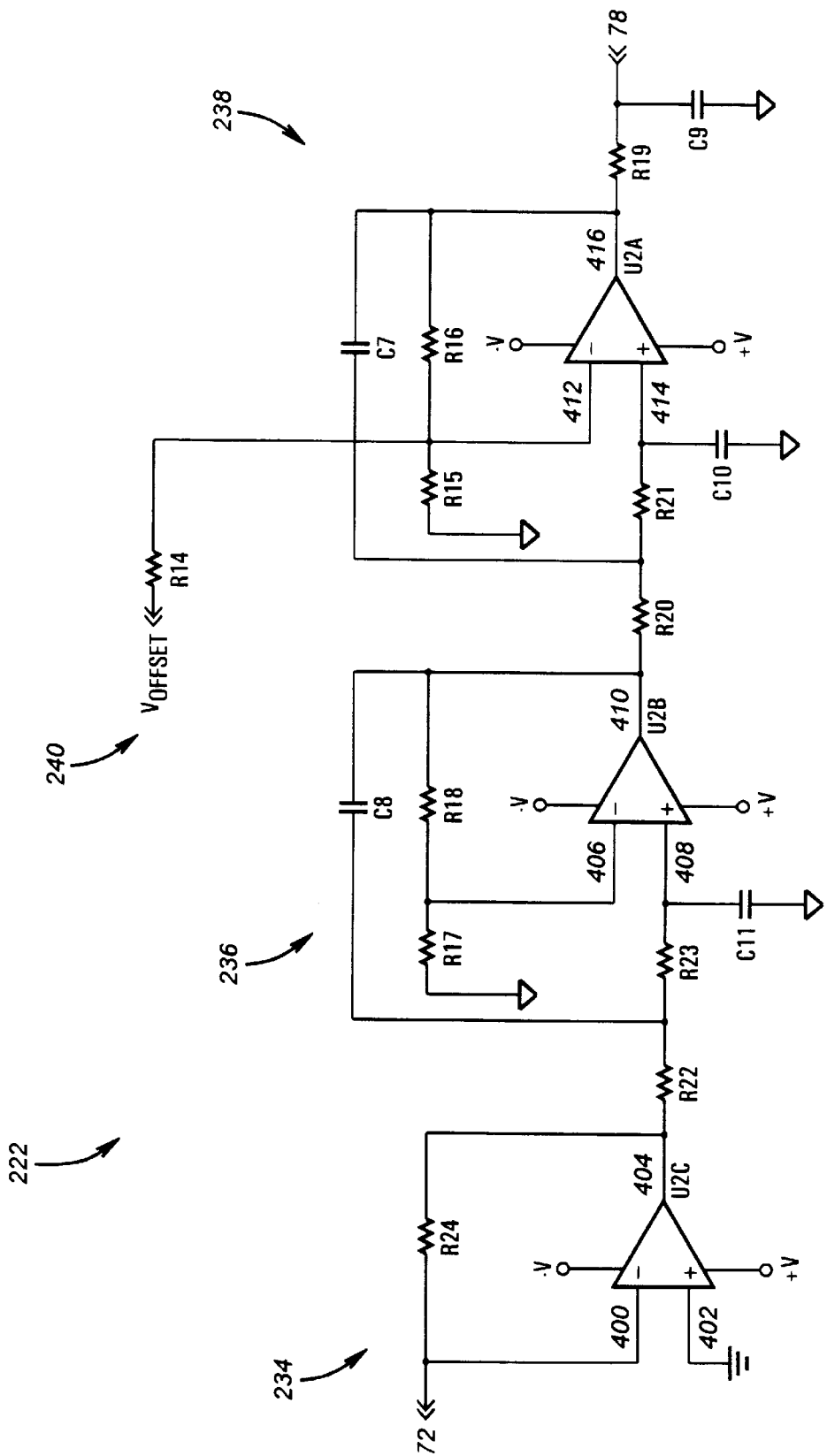
FIG. 9 is an exemplary circuit schematic of the signal conditioning circuitry of FIG. 5 for the offline forward detector of FIG. 6.
Figure 10:
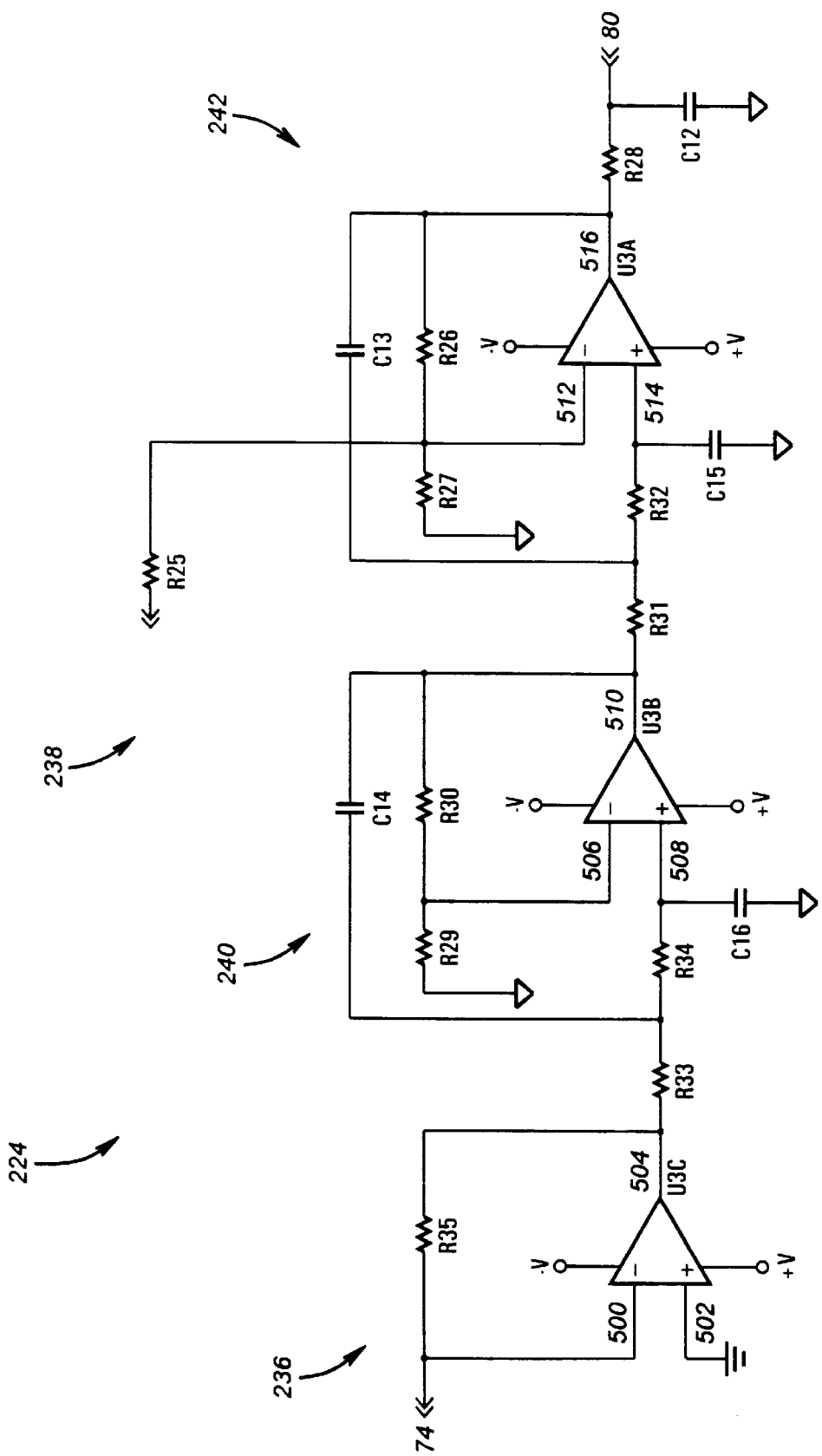
FIG. 10 is an exemplary circuit schematic of the signal conditioning circuitry of FIG. 5 for an offline backside detector of FIG. 6.

Referring to FIG. 9, an exemplary circuit schematic of signal conditioning circuitry 222 for the offline forward detector 100 is shown. The input signal to the signal conditioning circuitry 222 is the online forward detector signal 72. The online detector signal 72 is provided to an inverting terminal 400 of an operational amplifier U2C which uses current-to-voltage conversion to measure a short circuit current of the offline forward detector 100. A feedback network comprising a feedback resistor R24 is provided between the inverting terminal 400 and the output terminal 404 of the operational amplifier U2C. Further, the non-inverting terminal 402 of the operational amplifier U2C is coupled to ground.

The current-to-voltage conversion stage 234 is followed by a low pass filter stage 240. In the disclosed embodiment, the low pass filter stage 240 provides a fourth order Bessel low pass filter having a gain of four in the pass band and a cutoff frequency of approximately 0.2 hertz. The illustrated embodiment of the low pass filter stage 240 includes an operational amplifier U2B and an operational amplifier U2A, both having a capacitive/resistive feedback network. The non-inverting terminal 408 of the operational amplifier U2B is coupled to a capacitor C11 and a resistor R23. The resistor R23 is coupled to a resistor R22 which couples the current-to-voltage conversion stage 234 and the low pass filter stage 240. The inverting terminal 406 of the operational amplifier U2B is coupled to a feedback resistor R18 and a feedback resistor R17. The feedback resistor R17 is also coupled to ground. A feedback capacitor C8 is coupled between the output terminal 410 and a node defined between resistor R22 and R23.

The non-inverting terminal of the operation amplifier U2A is coupled to an input capacitor C10 and input resistor R21. The input resistor R21 is further coupled to a resistor R20 coupled to the output terminal 410 of the operational amplifier U2B. The inverting terminal 412 of the operational amplifier U2A is coupled to a feedback network 238 and also to an offset signal $V_{offSet}$ through a resistor R14.

The feedback network 238 includes a feedback resistor R16 and a feedback resistor R15 coupled to the inverting terminal 412 of the operational amplifier U2A. The feedback resistor R15 is also coupled to ground, and the feedback resistor R16 is also coupled to the output node 416. The feedback network 238 also includes a feedback capacitor C7 coupled between the output node 416 and a node defined between resistor R20 and resistor R21. The output node 416 is further coupled to a resistor RI 9 which is coupled to a capacitor C9 and a node forming the output signal 78.

Referring to FIG. 10, an exemplary circuit schematic of signal conditioning circuitry 224 for the offline backside detector 100 is shown. The input signal to the signal conditioning circuitry 224 is the offline backside detector signal 74. The offline backside detector signal 74 is provided to an inverting terminal 500 of an operational amplifier U3C which uses current-to-voltage conversion to measure a short circuit current of the offline backside detector 100. A feedback network comprising a feedback resistor R35 is provided between the inverting terminal 500 and the output terminal 504 of the operational amplifier U3C. Further, the non-inverting terminal 502 of the operational amplifier U3C is coupled to ground.

The current-to-voltage conversion stage 236 is followed by a low pass filter stage 240. In the disclosed embodiment, the low pass filter stage 240 provides a fourth order vessel low pass filter having a gain of four in the pass band and a cutoff frequency of approximately 0.2 hertz. The illustrated embodiment of the low pass filter stage 240 includes an operational amplifier U3B and an operational amplifier U3A, both having a capacitive and resistive feedback network. The non-inverting terminal 508 of the operational amplifier U3B is coupled to a capacitor C16 and a resistor R34. The resistor R34 is coupled to a resistor R33 which serves as a bridge between the current-to-voltage conversion stage 236 and the low pass filter stage 240. The inverting terminal 506 is coupled to a feedback resistor R30 and a feedback resistor R29. Feedback resistor R29 is also coupled to ground. A feedback capacitor C14 is coupled between the output terminal 510 and the common node of resistors R34 and R33.

The non-inverting terminal 514 of the operation amplifier U3A is coupled to an input capacitor C15 and input resistor R32. The input resistor R32 is further coupled to a resistor R31, which is also coupled to the output terminal 510 of the operational amplifier U3B. The inverting terminal 512 of the operational amplifier U1A is coupled to a feedback network 242 and also to an offset voltage, $V_{offSet}$ through resistor R25.

The feedback network 242 includes a feedback resistor R26 and a feedback resistor R27 coupled to the inverting terminal 512 of the operational amplifier U3A. The feedback resistor R27 is also coupled to ground, and the feedback resistor R26 is also coupled to the output node 516. The feedback network 242 also includes a feedback capacitor C13 coupled between the output node 516 and a node defined between resistor R31 and resistor R32. The output node 516 is further coupled to a resistor R28 which is coupled to a capacitor C12 and a node forming the output signal 80.

Referring to FIG. 11, an exemplary circuit schematic of current drive circuitry 75 for the emitter 94, temperature sensing circuitry 226, and power decoupling circuitry 244 is shown. The current drive circuitry 75 essentially provides a voltage-to-current circuit for driving the emitter 94. In the disclosed embodiment, the current drive circuitry 75 includes a pair of potentiometers P1 and P2, an operational amplifier U4 configured as a voltage-to-current converter, a transistor T1, and the emitter 94. The potentiometer P1 is connected to a register R44 coupled to a reference voltage $V_{ref}$. The potentiometer P2 is coupled to a capacitor C24 and a resistor R39. The resistor R39 is connected to a capacitor C23 coupled to an inverting terminal 246 of the operational amplifier U4 and to a test input signal, TEST_INPUT, used for detecting a frequency response. A non-inverting terminal 248 is coupled to a resistor R46 which is coupled to a resistor R42 and the emitter 94. In the disclosed embodiment, the emitter 94 is a light emitting diode for converting current to infrared light. The resistor R42 and the capacitor C24 are further coupled to a power supply ground VCC_GND. The output terminal 250 of the operational amplifier U4 is coupled to a resistor R40, which is coupled to a base of the transistor T1. In the disclosed embodiment, the transistor T1 is a bipolar junction transistor. The collector of the transistor T1 is coupled to a resistor R41 which is coupled to a capacitor C22. The capacitor C22 is further coupled to a power supply ground VCC_GND. The emitter of the transistor T1 is coupled to the emitter 94 of the narrow band water cut meter 32. In the disclosed configuration, the transistor T1 thus serves as a current controlled switch, and the current drive circuitry 75 drives the emitter 94 with a current proportional to the voltage influenced by the potentiometers P1 and P2.

The power decoupling circuitry 244 is of a conventional type having advantages appreciated by one of ordinary skill in the art. In the disclosed embodiment, a +5V power supply and a +15V power supply are provided. In the disclosed embodiment of the power decoupling circuitry 244, an input node 252, which is a positive terminal of a +15V power supply, is coupled to a capacitor C18 and a capacitor C19 having a parallel relationship. Both the capacitor C18 and the capacitor C19 are further coupled to a capacitor C21 and a capacitor C20. The capacitors C21 and C20 are coupled to another input node 254, which is a negative terminal of a +15V power supply. Capacitor C18 and capacitor C21 are coupled to a resistor R38 which couples the 15V power supply ground VCC_GND to the signal ground SIGNAL_GND. The capacitor C19 and capacitor C20 are further coupled to a resistor R37. The resistor R37 couples the 15V power supply ground to the 5V power supply ground. Capacitor C17 has a parallel relationship with the voltage $V_{ref}$ and is coupled to a node 256, which is the positive terminal of the +15V power supply.

The temperature sensing circuitry 226 is used for sensing the temperature of the emitter 94. In the disclosed embodiment, the temperature sensing circuitry 226 includes a temperature sensor 258 which is coupled to a resistor R45. An output terminal 260 of the circuit is coupled to the temperature sensor 258 and the resistor R45. The output terminal 260 provides an output signal EMITTER_TEMP, representing the temperature of the emitter 94. The resistor R45 is further coupled to a signal ground SIGNAL_GND.

Figure 12:
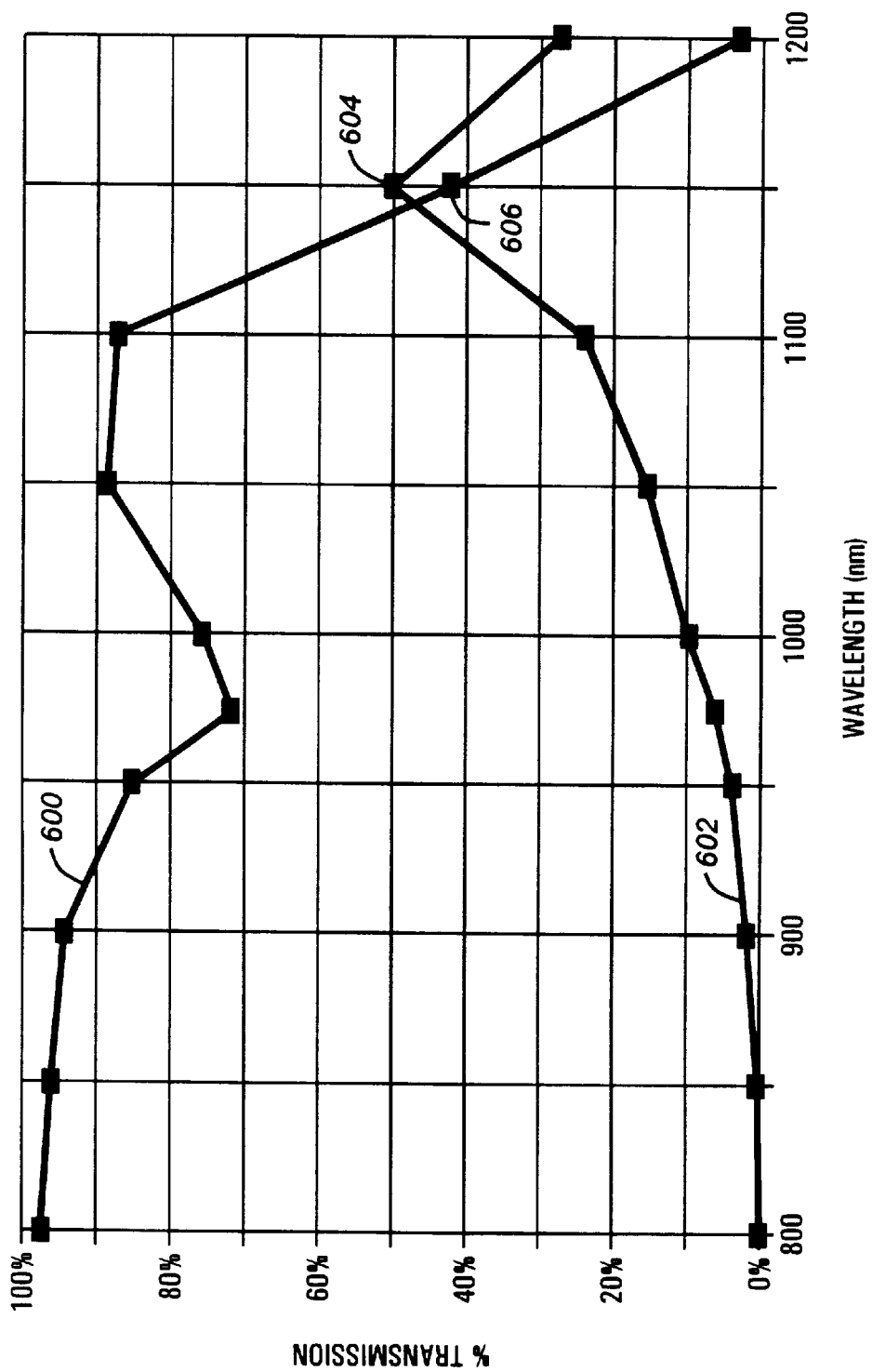
FIG. 12 is a graph diagram illustrating the transmission properties of oil and water for a near to mid infrared region including a narrow infrared band in which light is emitted by the narrow band infrared water cut meter of FIG. 5.

Referring to FIG. 12, a graph diagram illustrating the transmission or spectral properties of oil and water for a section of the near infrared region including a narrow infrared band in which light is emitted by the narrow band infrared water cut meter 32 is shown. In accordance with the present invention, the emitter 94 of the narrow band infrared water cut meter 32 emits a narrow band of infrared light selected from the near infrared region. In one embodiment of the narrow band infrared water cut meter 32, a wavelength is selected at which the transmission characteristic of water is substantially different from the transmission characteristic of oil. The selected wavelength thus provides for differentiation of oil content and water content of the flow stream 84. Further, at the selected wavelength, the transmission characteristic of water is essentially the same as the transmission characteristic for gas. The narrow band infrared water cut meter 32 thus does not confuse gas for oil at the selected wavelength. It has been found that at a wavelength on the order of 950 nanometers, the transmission characteristic for water is substantially different from the transmission characteristic for oil. For example, at 950 nanometers in the illustrated diagram, the transmission curve 600 for oil has a substantially greater percentage of infrared signal transmission than a transmission curve 602 for water. It should be understood that wavelengths in the near to mid infrared region having a like effect may also be selected.

In another embodiment of the narrow band infrared water cut meter 32, a wavelength is selected at which the transmission characteristic for oil is substantially different from the transmission characteristic for gas and the transmission characteristic for oil is essentially the same as the transmission characteristic for water. At such a wavelength, a narrow band of infrared light is substantially absorbed by the oil content and water content of the flow stream 84 and substantially transmitted by the gas content of the flow stream 84. This embodiment thus allows for gas to be differentiated from oil and water. It has been found that a wavelength of 1140 nanometers is such a wavelength at which a narrow band of infrared light is substantially absorbed by oil content and water content and substantially transmitted by gas content. The proximity of the datapoint 604 of the transmission curve for water and the datapoint 606 of the transmission curve for oil near the wavelength of 1140 nanometers serves to illustrate the special property of this embodiment of the narrow band water cut meter 32.

Figure 13:
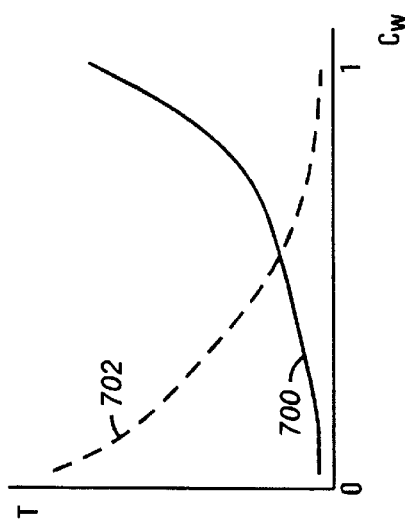
FIG. 13 is a graph diagram illustrating signal transmission for a detector of the narrow band infrared water cut meter of FIG. 5 as a function of the water cut of the flow stream of FIG. 5.

Referring to FIG. 13, a graph diagram illustrating signal transmission for a detector of the narrow band infrared water cut meter 32 as a function of the water cut of the flow stream 48 is shown. Transmission curve 700 represents the logarithmic relationship between the water cut $C_W$ of the flow stream 44 and transmission by a detector signal of the narrow band infrared water cut meter 32 over a full water cut range. Conventional water cut meters such as microwave water cut meters have measurement sensitivity on the low water cut end. An exemplary transmission curve 702 for a microwave water cut meter indicated schematically in broken line is shown. For many well testing applications, however, sensitivity on the high water cut end is needed. This need is met by the narrow band infrared water cut meter 32 which provides sensitivity on the high water cut end as opposed to the low water cut end. An exemplary transmission curve 700 for the narrow band infrared water cut meter 32 is shown. Sensitivity on the high water cut end provides for better accuracy with flow compositions having a high percentage of water content.

Figure 14:
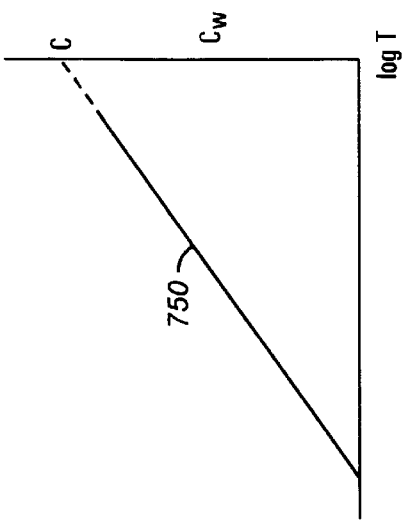
FIG. 14 is a graph diagram illustrating an exemplary water cut of a flow stream as a function of the logarithm of signal transmission for a detector of the narrow band infrared water cut meter of FIG. 5.

Referring to FIG. 14, a graph diagram illustrating water cut of the flow stream 44 as a function of a logarithm of signal transmission for a detector of the narrow band infrared water cut meter 32 is shown. Like FIG. 13, the linear water cut curve 750 of FIG. 14 serves to illustrate the logarithmic relationship between transmission for a detector signal of the narrow band infrared water cut meter 32 and the water cut of the flow stream 44. The slope of the water cut curve 750 corresponds to A calibration constant value, and the vertical axis intercept value of the curve 750 corresponds to the C calibration constant value.

Figure 16:
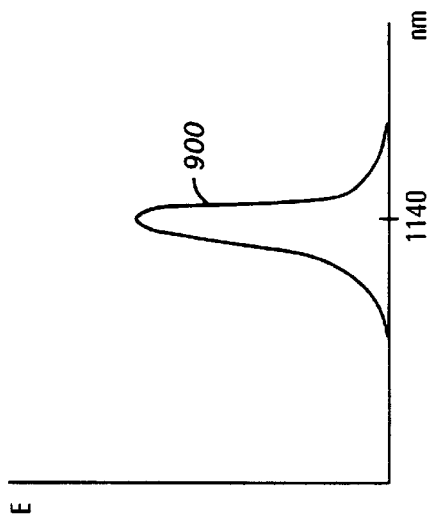
FIGS. 15 and 16 are graph diagrams illustrating an exemplary light emission by the emitter of FIG. 6 over exemplary wavelength ranges.
Figure 15:
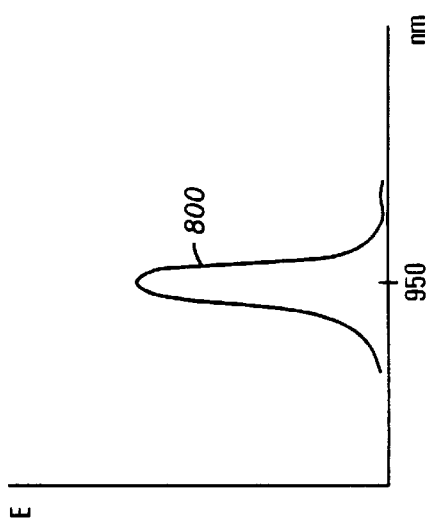

Referring to FIG. 15, a graph diagram illustrating an exemplary light emission by the emitter 94 over an exemplary wavelength range is shown. FIG. 16 is also a graph diagram illustrating an exemplary light emission by the emitter 94 over an exemplary wavelength range. The light emission 800 is centered at a wavelength of 950 nanometers, and the light emission 900 is centered at a wavelength of 1140 nanometers. The light emission 800 represents a narrow band of light which is substantially transmitted through water content and gas content and is substantially absorbed by oil content, and light emission 900 represents a narrow band of infrared light which is substantially absorbed by oil content and water content and substantially transmitted by gas content.

Thus, the narrow band infrared water cut meter provides for a full range water cut detection independent of entrained gas for a host of applications. It should be understood that the applications described herein are exemplary and not exhaustive. For example, another application would be providing the narrow band water cut meter 32 downhole in a package suitable for downhole water cut measurements, eliminating the need to bring up, separate for testing, and then reinject a flow stream. Further, it should be understood that the location, placement, position, or environment of the water cut meter or any of its components may be varied.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

What is claimed is:

1. A narrow band infrared water cut meter, comprising:
  a light source probe for emitting a narrow band of infrared light of a predetermined wavelength to a three-phase flow stream; and
  a light detector probe for detecting attenuation of the narrow band of infrared light by the three-phase flow stream,
  wherein the narrow band of infrared light of the predetermined wavelength is substantially transmitted through a first phase and a second phase of the three-phase flow stream and substantially absorbed by a third phase of the three-phase flow stream, and
  wherein a water cut of the flow stream is determined by the attenuation of the narrow band of infrared light by the three-phase flow stream.

2. The water cut meter of claim 1, wherein the three phase flow stream includes an oil content, a gas content, and a water content, and wherein the narrow band of infrared light of the predetermined wavelength is substantially transmitted through the water content and the gas content and substantially absorbed by the oil content.

3. The water cut meter of claim 1, wherein the predetermined wavelength is in the range of 800 to 1200 nm.

4. The water cut meter of claim 3, wherein the predetermined wavelength is approximately 950 nm.

5. The water cut meter of claim 1, the light source probe further comprising:
  an emitter for emitting the narrow band of infrared light to the flow stream; and
  an offline backside detector for detecting reflectance of the narrow band of infrared light by the flow stream.

6. The water cut meter of claim 1, the light detector probe comprising:
  an online forward detector for detecting absorption of the narrow band of infrared light by the flow stream.

7. The water cut meter of claim 6, the light detector probe further comprising:
  an offline forward detector for detecting scattering of the narrow band of infrared light by the flow stream.

8. The water cut meter of claim 1, wherein the narrow band of infrared light is substantially absorbed by the oil content and the water content and substantially transmitted by the gas content.

9. A narrow band infrared water cut system, comprising:
  a narrow band infrared water cut meter, comprising:
    a light source probe for emitting a narrow band of infrared light of a predetermined wavelength to a three-phase flow stream; and
    a light detector probe for detecting attenuation of the narrow band of infrared light by the three-phase flow stream,
    wherein the narrow band of infrared light of the predetermined wavelength is substantially transmitted through a first phase and a second phase of the three-phase flow stream and substantially absorbed by a third phase of the three-phase flow stream, and
    wherein a water cut of the three-phase flow stream is determined by the attenuation of the narrow band of infrared light by the three-phase flow stream;
  a signal conditioning block for generating a temperature sensing signal and an absorption signal representing absorption of the narrow band of infrared light by the flow stream; and
  a flow computer for processing the temperature sensing signal and the absorption signal to determine a water cut of the flow stream.

10. The water cut system of claim 9, the light source probe detecting reflectance of the narrow band of infrared light by the flow stream, wherein the signal conditioning block generates a reflectance signal representing reflectance of the narrow band of infrared light by the flow stream and wherein the flow computer processes the reflectance signal as a step in determining the water cut of the flow stream.

11. The water cut system of claim 9, the light detector probe detecting scattering of the narrow band of infrared light by the flow stream, wherein the signal conditioning block generates a scattering signal representing scattering of the narrow band of infrared light by the flow stream and wherein the flow computer processes the scattering signal as a step in determining the water cut of the flow stream.

12. A narrow band infrared well line testing system comprising:
  a well line providing a flow stream having a water content, oil content, and gas content;
  a first narrow band infrared water cut meter for emitting to the flow stream a narrow band of infrared light of a first predetermined wavelength substantially transmitted through the water content and the gas content and substantially absorbed by the oil content; and
  a second narrow band infrared water cut meter for receiving the flow stream from the first narrow band water cut meter and emitting to the flow stream a narrow band of infrared light of a second predetermined wavelength substantially absorbed by the oil content and the water content and substantially transmitted by the gas content.

13. The well testing system of claim 12, wherein the first predetermined wavelength is approximately 950 nm.

14. The well testing system of claim 12, wherein the second predetermined wavelength is approximately 1140 nm.

15. The well testing system of claim 12, wherein the first predetermined wavelength and the second predetermined wavelength are in the range of 800 to 1200 nm.

16. The well testing system of claim 12, wherein the first narrow band infrared water cut meter indicates a fraction of the oil content and the second narrow band infrared water cut meter indicates a fraction of the gas content and a fraction of the water content.

17. A method of measuring concentration of a tri-phase flow stream at a well line using a first narrow band infrared water cut meter and a second narrow band infrared water cut meter, comprising the steps of:
  flowing a tri-phase flow stream to the first narrow band infrared water cut meter;
  emitting a narrow band infrared light of a first predetermined wavelength substantially transmitted through a first phase and a second phase and substantially absorbed by a third phase to the tri-phase flow stream by the first narrow band infrared water cut meter;

detecting attenuation of the narrow band of infrared light of the first predetermined wavelength by the first narrow band infrared water cut meter;

flowing the tri-phase flow stream from the first narrow band infrared water cut meter to the second narrow band infrared water cut meter;

emitting a narrow band of light of a second predetermined wavelength substantially absorbed by the first phase and the third phase and substantially transmitted by the second phase to the tri-phase flow stream by the second narrow band infrared water cut meter; and detecting attenuation of the narrow band of infrared light of the second predetermined wave length by the second narrow band water cut meter.

18. The method of claim 17, further comprising the step of:

measuring the mass flow rate of the three-phase flow stream.

19. The method of claim 17, wherein the tri-phase flow stream comprises a gas phase, a water phase and an oil phase.

20. A method of measuring concentration of a tri-phase flow stream at a well testing satellite with a narrow band infrared water cut meter, comprising the steps of:

separating the tri-phase flow stream into a single-phase flow stream and a substantially two-phase flow stream;

flowing the two-phase flow stream through the narrow band infrared water cut meter;

emitting a narrow band of infrared light of a predetermined wavelength substantially transmitted through a first phase and a second phase of the substantially two-phase flow stream and substantially absorbed by a third phase of the substantially two-phase flow stream by the narrow band infrared water cut meter to the two-phase flow stream; and detecting attenuation of the narrow band of infrared light by the two-phase flow stream by the narrow band infrared water cut meter.

21. The method of claim 20, further comprising the step of:

measuring a flow rate of the two-phase flow stream.

22. The method of claim 20, further comprising the step of:

measuring a flow rate of the single-phase flow stream.

23. The method of claim 20, wherein the single-phase flow stream comprises gas content and the two-phase flow stream comprises oil content and water content.

24. A method of measuring concentration of a tri-phase flow stream at a well line using a narrow band infrared water cut meter, comprising the steps of:

diverting a tri-phase flow stream from a well line to a two-phase separator;

separating the tri-phase flow stream into a single-phase flow stream and a substantially two-phase flow stream;

flowing the substantially two-phase flow stream through the narrow band infrared water cut meter;

emitting a narrow band of infrared light of a predetermined wavelength substantially transmitted through a first phase and a second phase of the substantially two-phase flow stream and substantially absorbed by a third phase of the substantially two-phase flow stream by the narrow band infrared water cut meter to the two-phase flow stream; and detecting attenuation of the narrow band of infrared light by the substantially two-phase flow stream by the narrow band infrared water cut meter.

25. The method of claim 24, wherein the single-phase flow stream comprises gas content and the two-phase flow stream comprises oil content and water content.

\* \* \* \* \*